(12) United States Patent
Holmqvist et al.

(10) Patent No.: US 11,331,432 B2
(45) Date of Patent: May 17, 2022

(54) ADMINISTRATION ASSEMBLY FOR A MEDICAMENT DELIVERY DEVICE AND A MEDICAMENT DELIVERY DEVICE COMPRISING THE SAME

(71) Applicant: SHL MEDICAL AG, Zug (CH)

(72) Inventors: Anders Holmqvist, Värmdö (SE); Pär Leander, Nacka (SE); Linda Odelberg, Ekerö (SE); Erika André, Saltsjö-Boo (SE)

(73) Assignee: SHL MEDICAL AG, Zug (CH)

( * ) Notice: Subject to any disclaimer, the term of this patent is extended or adjusted under 35 U.S.C. 154(b) by 192 days.

(21) Appl. No.: 16/630,378

(22) PCT Filed: Jul. 2, 2018

(86) PCT No.: PCT/EP2018/067774
§ 371 (c)(1),
(2) Date: Jan. 10, 2020

(87) PCT Pub. No.: WO2019/011688
PCT Pub. Date: Jan. 17, 2019

(65) Prior Publication Data
US 2020/0197618 A1 Jun. 25, 2020

(30) Foreign Application Priority Data

Jul. 12, 2017 (EP) ..................... 17180895

(51) Int. Cl.
*A61M 5/315* (2006.01)
*A61M 5/20* (2006.01)

(52) U.S. Cl.
CPC ...... *A61M 5/31501* (2013.01); *A61M 5/2033* (2013.01); *A61M 2005/208* (2013.01); *A61M 2005/31508* (2013.01)

(58) Field of Classification Search
CPC ............ A61M 5/2033; A61M 5/31501; A61M 2005/208; A61M 5/3243; A61M 5/20;
(Continued)

(56) References Cited

U.S. PATENT DOCUMENTS 5,300,030 A * 4/1994 Crossman ........... A61M 5/2033
604/134
2013/0317432 A1 11/2013 Fabien et al.
(Continued)

FOREIGN PATENT DOCUMENTS

CN 103442756 A 12/2013
CN 103945879 A 7/2014
(Continued)

OTHER PUBLICATIONS

YpsoMate, The 2-Step Autoinjector, Apr. 2, 2021, Ypsomed Devliery Systems, Web Page. (Year: 2021).*

*Primary Examiner* — Quynh-Nhu H. Vu
(74) *Attorney, Agent, or Firm* — McDonnell Boehnen Hulben & Berghoff LLP

(57) ABSTRACT

An administration assembly is presented having a plunger rod, a first resilient member biasing the plunger rod, an elongated plunger rod holder configured to receive the plunger rod, an activation sleeve receiving a portion of the plunger rod holder, and configured to move axially from a first position relative to the plunger rod holder to a second position. The activation sleeve is biased towards the first position and the plunger rod holder has a first and second hold and release structure, wherein in the first position the activation sleeve is configured to maintain the first hold and release structure in an axially locking contact position with the second hold and release structure in which the second hold and release structure is prevented from movement relative to the first hold and release structure, thereby
(Continued)

locking the plunger rod axially relative to the plunger rod holder.

16 Claims, 10 Drawing Sheets

(58) Field of Classification Search
CPC .................. A61M 5/24; A61M 5/326; A61M 2005/2073; A61M 5/31565; A61M 5/31566; A61M 5/31576; A61M 5/31578; A61M 5/3158; A61M 2005/31508
See application file for complete search history.

(56) References Cited

U.S. PATENT DOCUMENTS

| | | | |
|---|---|---|---|
| 2015/0273162 A1* | 10/2015 | Holmqvist | A61M 5/2033 604/111 |
| 2016/0008541 A1* | 1/2016 | Hirschel | A61M 5/24 604/506 |
| 2017/0165428 A1 | 6/2017 | Sall | |

FOREIGN PATENT DOCUMENTS

| | | |
|---|---|---|
| CN | 104136057 A | 11/2014 |
| CN | 105102022 A | 11/2015 |
| CN | 105188807 A | 12/2015 |
| CN | 105246528 A | 1/2016 |
| CN | 105263545 A | 1/2016 |
| CN | 105492042 A | 4/2016 |
| CN | 105517600 A | 4/2016 |
| CN | 106029133 A | 10/2016 |
| CN | 106132458 A | 11/2016 |
| CN | 106255522 A | 12/2016 |
| JP | 2016-512766 A | 5/2016 |
| WO | 2010/081489 A1 | 7/2010 |
| WO | 2011/043714 A1 | 4/2011 |
| WO | 2013/167494 A1 | 11/2013 |
| WO | 2014/195183 A1 | 12/2014 |
| WO | 2015/197867 A1 | 12/2015 |

* cited by examiner

ADMINISTRATION ASSEMBLY FOR A MEDICAMENT DELIVERY DEVICE AND A MEDICAMENT DELIVERY DEVICE COMPRISING THE SAME

CROSS REFERENCE TO RELATED APPLICATIONS

The present application is a U.S. National Phase Application pursuant to 35 U.S.C. § 371 of International Application No. PCT/EP2018/06777 filed Jul. 2, 2018, which claims priority to European Patent Application No. 17180895.9 filed Jul. 12, 2017. The entire disclosure contents of these applications are herewith incorporated by reference into the present application.

TECHNICAL FIELD

The present disclosure generally relates to medical devices. In particular, it relates to an administration assembly for a medicament delivery device, and to a medicament delivery device comprising an administration assembly.

BACKGROUND

Medicament delivery devices, in particular automated administration devices such as auto-injectors, are typically spring-biased. A device of this type may be activated for example by pushing the device towards the injection site, whereby a delivery member cover is moved in the proximal direction further into the housing, causing the device activation, or by means of an external button or slider.

WO2011043714 discloses a medicament delivery device comprising a housing, a first activator member, a second activator member, a drive mechanism including a plunger rod and a first compression spring, and a needle shield sleeve. The second activator comprises proximally extending flexible tongues configured to engage with the plunger rod to retain the plunger rod in an axial position prior to activation. This engagement is obtained due to the first activator member, which circumferentially encloses the flexible tongues and delimits the radial movement by the flexible tongues. The flexible tongues are thus prevented from flexing radially outwards. The first activator member is configured to be moved in the distal direction inside the housing by the needle shield sleeve, away from the flexible tongues, allowing the flexible tongues to flex radially outwards to disengage from the plunger rod. The plunger rod is thereby able to travel in the proximal direction.

Prior to use, the flexible tongues are thus subjected to the forward-biasing force provided by the first compression spring in a manner, causing the flexible tongues to weaken over time. This mechanical weakening is obtained because the cross-sectional dimension of the flexible tongues is reduced over time. Thus, if for example the medicament delivery device is kept in storage for a longer period of time, for example a couple of years, the plastic structure of the flexible tongues may be substantially weakened. The first compression spring will therefore have to be designed to provide a forward-biasing force which does not cause damage to the flexible tongues even after a long period of storage.

SUMMARY

There has been a trend towards liquid medicaments with higher viscosity. This trend has been driven due to medicaments which nowadays contain larger molecules than in the past. Such medicaments are typically biosimilars. To be able to expel medicaments with higher viscosity, a higher biasing force on the plunger rod is required. It would therefore be desirable to be able to provide a high plunger rod biasing.

In view of the above, a general object of the present disclosure is to provide an administration assembly for a medicament delivery device which solves or at least mitigates problems of the prior art.

There is hence according to a first aspect of the present disclosure provided an administration assembly for a medicament delivery device, comprising: a plunger rod, a first resilient member configured to bias the plunger rod in the proximal direction, an elongated plunger rod holder configured to receive the plunger rod, an activation sleeve configured to receive a portion of the plunger rod holder, and configured to move axially from a first position relative to the plunger rod holder to a second position, wherein the activation sleeve is configured to be biased towards the first position, wherein the plunger rod holder has a first hold and release structure and the plunger rod has a second hold and release structure, wherein in the first position the activation sleeve is configured to maintain the first hold and release structure in an axially locking contact position with the second hold and release structure in which the second hold and release structure is prevented from movement relative to the first hold and release structure, thereby locking the plunger rod axially relative to the plunger rod holder, wherein in the second position the activation sleeve is configured to allow the first hold and release structure to move from the axially locking contact position, whereby biasing of the plunger rod provided by the first resilient member causes the second hold and release structure to act with a proximally directed force on the first hold and release structure, moving the first hold and release structure tangentially from the axially locking contact position to thereby release the plunger rod from the plunger rod holder.

According to one embodiment the triggering member is a delivery member cover having a distal end configured to bear against a proximal end of the activation sleeve.

The triggering member could alternatively for example be a push button or a slider.

One embodiment comprises a second resilient member configured to bias the activation sleeve in the proximal direction towards the first position.

One embodiment comprises a guiding structure configured to prevent the plunger rod to rotate relative to the plunger rod holder when released from the plunger rod holder.

According to one embodiment the second hold and release structure defines the guiding structure.

According to one embodiment the second hold and release structure is a radially outwards extending protrusion, and wherein the first hold and release structure includes a first tangential tab which in the axially locking contact position of the first hold and release structure is configured to be axially aligned with and proximally located relative to the second hold and release structure.

According to one embodiment the first tangential tab has a distal end face configured to cooperate with the second hold and release structure, wherein the distal end face of the first tangential tab is bevelled in the tangential direction.

Due to the bevelled structure of the first tangential tab, the second hold and release structure is able to move the first tangential tab in the tangential direction as a result of the forward, or proximal, biasing of the plunger rod.

According to one embodiment the first hold and release structure includes a distally extending axial first arm, wherein the first tangential tab is provided on a distal portion of the first arm.

The first arm has an extension in the distal direction. The first arm hence extends towards the rear end, or distal end, of the administration assembly. The first arm thus has an attachment, or joins the body of the plunger rod holder, at a proximal location of the plunger rod holder relative to the first tangential tab, forms a distal end portion of the first arm.

Thus, contrary to the prior art solution, the first arm will initially be in a compressed state. The first arm will thus not be subjected to a pulling force when the activation sleeve is in the first position, and consequently, there the first arm will not become mechanically weakened if stored for a longer period of time.

According to one embodiment the activation sleeve comprises an axially extending rib configured to bear against the first arm in the first position of the activation sleeve to prevent movement of the first arm in the tangential direction and to move axially in the distal direction beyond the first arm in the second position of the activation sleeve, allowing the first arm to move in the tangential direction to thereby allow the second hold and release structure to move axially past the first tangential tab.

According to one embodiment the plunger rod holder has an axially extending second slot in which the second hold and release structure is configured to run in the proximal direction when the plunger rod has been released from the plunger rod holder. Relative rotation between the plunger rod and the plunger rod holder may thereby be prevented when the plunger rod is moved proximally relative to the plunger rod holder.

According to one embodiment the first hold and release structure comprises a distally extending axial second arm extending parallel with the first arm, which second arm has a second tangential tab extending towards the first tangential tab, and wherein the radially outwards extending protrusion is configured to bear against and be located distally with respect to the first tangential tab and the second tangential tab when the activation sleeve is in the first position, the first tangential tab and the second tangential tab blocking proximal movement of the plunger rod.

According to one embodiment the activation sleeve comprises a plurality of axially extending ribs, wherein a first axially extending rib is configured to bear against the first arm and a second axially extending rib is configured to bear against the second arm in the first position of the activation sleeve to prevent tangential movement of the first arm and the second arm, the first axially extending rib and the second axially extending rib being configured to move axially in the distal direction beyond the first arm and the second arm in the second position of the activation sleeve, allowing the first arm and the second arm to move in the tangential direction to thereby allow the radially outwards extending protrusion to move axially past the first tangential tab and the second tangential tab.

According to one embodiment the activation sleeve has a radially flexible tongue configured to lock the activation sleeve in the first position when the activation sleeve has returned from the second position to the first position by biasing force exerted on the activation sleeve by a second resilient member.

According to one embodiment the radially flexible tongue is configured to bear against the radially outwards extending protrusion of the plunger rod when the activation sleeve is in the first position.

According to one embodiment the radially flexible tongue is configured to move over the radially outwards extending protrusion when moved from the first position towards the second position.

According to one embodiment the radially flexible tongue has a radially inwards extending protrusion and the first arm and the second arm have radial heels, wherein when the activation sleeve is returned to the first position, the radially inwards extending protrusion is arranged proximally and facing the radial heels to prevent the activation sleeve from being moved in the distal direction.

There is according to a second aspect of the present disclosure provided a medicament delivery device comprising: a housing, a triggering member configured to move the activation sleeve from the first position towards the second position, and an administration assembly according to the first aspect presented herein, configured to be received by the housing.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

Figure 1:
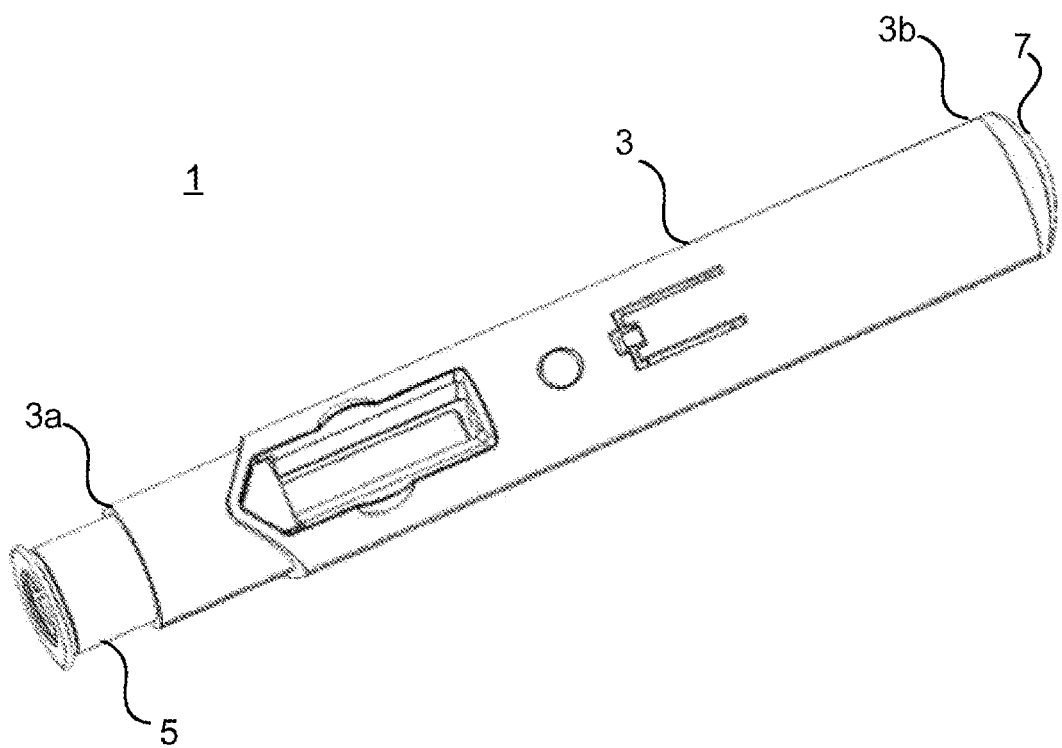
FIG. 1 is a perspective view of an example of a medicament delivery comprising an administration assembly.

FIG. 1 shows a perspective view of an example of a medicament delivery device 1. The exemplified medicament delivery device 1 is an auto-injector comprising an administration assembly, not shown, as will be described in more detail in what follows.

The medicament delivery device 1 comprises a housing 3 having a proximal end 3a and a distal end 3b, a delivery member cover 5 extending from a proximal opening in the proximal end 3a of the housing 3, and a rear end cap 7.

The delivery member cover 5 is biased in the proximal direction. The delivery member cover 5 is configured to be moved linearly, or axially, relative to the housing 3. The delivery member cover 5 is configured to be moved between an extended position relative to the housing 3, shown in FIG. 1, and a retracted position relative to the housing 3. In the retracted position, a greater portion of the delivery member cover 5 is received by the housing 3 than in the extended position. The delivery member cover 5 is configured to be biased towards the extended position.

Figure 2:
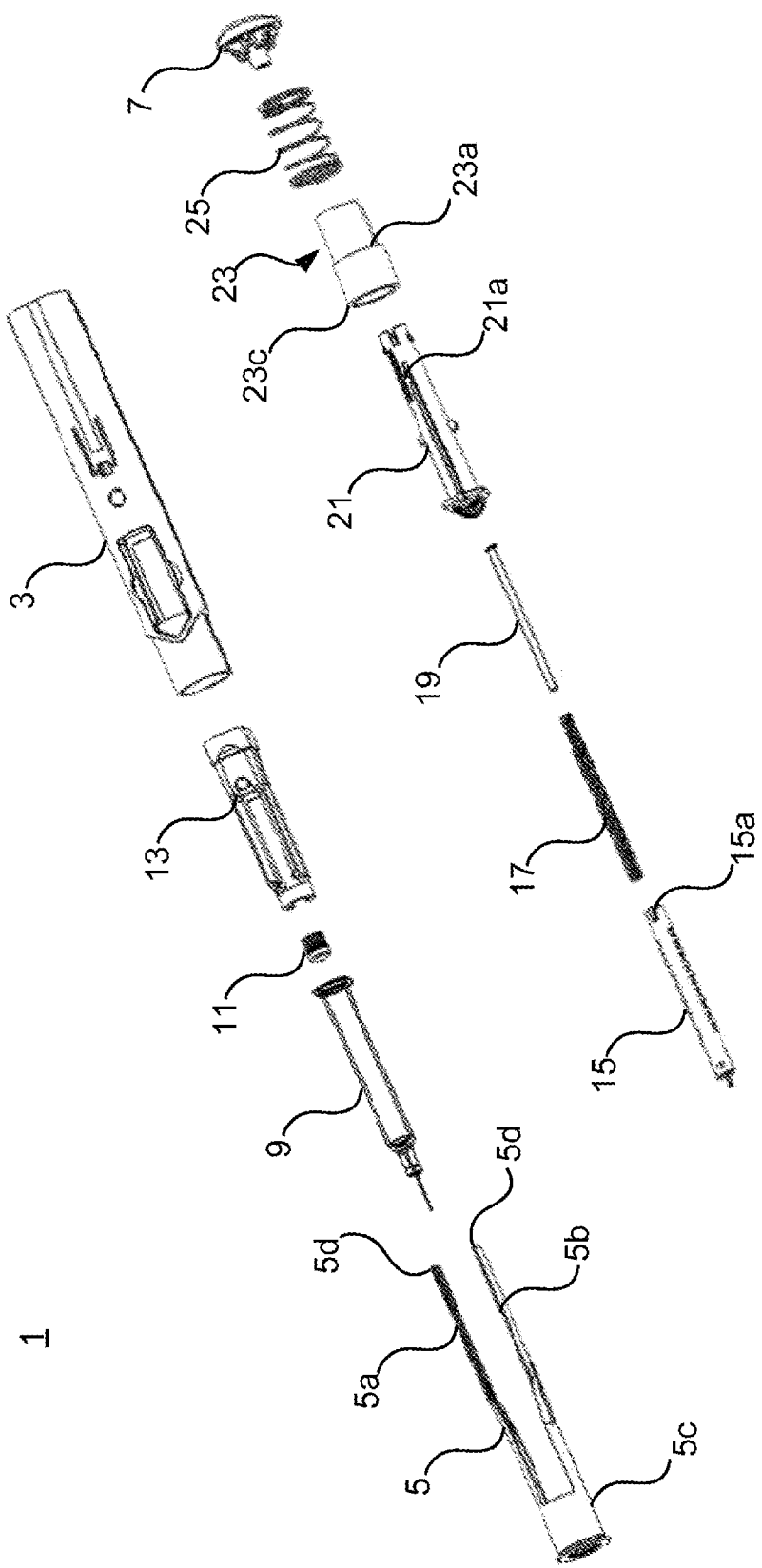
FIG. 2 shows an exploded view of the medicament delivery device in FIG. 1.

FIG. 2 shows an exploded view of the medicament delivery device 1. The delivery member cover 5 has a first delivery member cover arm 5a and a second delivery member cover arm 5b, and a cylindrical proximal portion 5c configured to extend from the housing 3 in the extended position of the delivery member cover 5. The first delivery member cover arm 5a and the second delivery member cover arm 5b extend in the distal direction from the proximal portion 5c.

In a fully mounted state, the medicament delivery device 1 may comprise a medicament container 9, a stopper 11 and a medicament container holder 13. The medicament container holder 13 is mounted in the housing 3 and configured to hold the medicament container 9. The medicament container 9 is configured to receive the stopper 11 through an open distal end thereof.

The medicament delivery device 1 further comprises an administration assembly 10 including a plunger rod 15, a first resilient member 17, for example a spring, a guide rod 19, a plunger rod holder 21, an activation sleeve 23 and a second resilient member 25, for example a spring. The administration assembly 10 also includes a triggering member, here exemplified by the delivery member cover 5.

The plunger rod holder 21 is configured to receive the plunger rod 15. The plunger rod has 15 has an inner axial channel, not shown. The first resilient member 17 is configured to be received by the plunger rod 15. In particular, the first resilient member 17 is configured to be received in the axial channel of the plunger rod 15. The first resilient member 17 is configured to receive the guide rod 19 when arranged in the axial channel. Bending of the highly stiff first resilient member 17 can thus be prevented.

The plunger rod 15 has a second hold and release structure 15a provided on a distal end portion of the outer surface of the plunger rod 15. In the present example, the second hold and release structure 15a includes a radially outwards extending protrusion, or wing.

The plunger rod holder 21 is configured to receive the plunger rod 15. Prior to use of the medicament delivery device 1, the plunger rod 15 is prevented from moving axially in the proximal direction relative to the plunger rod holder 21. Hereto, the plunger rod holder 21 has a first hold and release structure 21a configured to cooperate with the second hold and release structure 15a of the plunger rod 15. Prior to medicament administration, the first hold and release structure 21a is configured to be maintained by the activation sleeve 23 in an axially locking contact position with the second hold and release structure 15a.

The activation sleeve 23 is essentially cylindrical and configured to receive a portion of the plunger rod holder 21. The activation sleeve 23 is configured to be moved axially relative to the plunger rod holder 21 from an initial position to a release position located distally relative to the initial position. The activation sleeve 23 is configured to circumferentially enclose the plunger rod holder 21 and to cooperate with the first hold and release structure 21a.

The activation sleeve 23 is configured to be moved by a triggering member, which in the present example is the delivery member cover 5, from the initial position to the release position. In particular, the delivery member cover 5 has a distal end 5d configured to bear against a proximal end 23c of the activation sleeve 23. In the present example, the first delivery member cover arm 5a and the second delivery member cover arm 5b are configured to bear against the proximal end of the activation sleeve 23. When the activation sleeve 23 has been moved in the distal direction, to the release position, the first hold and release structure 21a is allowed to move from the axially locking contact position with the second hold and release structure 15a. The axially locking contact position of the first hold and release structure 21a with the second hold and release structure 15a is what maintains the plunger rod 15 in an axially interlocked state with the plunger rod holder 21. The plunger rod 15 will thus be allowed to move in the proximal direction, into the medicament container 9. A medicament contained therein may thereby be expelled.

The second resilient member 25 is configured to bias the activation sleeve 23 in the proximal direction. Due to this biasing, the activation sleeve 23 bears against the distal end 5*d* of the delivery member cover 5. According to the present example, the activation sleeve 23 has an outer surface provided with a flange 23*a*. The second resilient member 25 is configured to be mounted to bear against the flange 23*a* and the rear end cap 7. The second resilient member 25 will thus bias the activation sleeve 23 proximally so that the proximal end 23*c* of the activation sleeve 23 contacts the distal end 5*d* of the delivery member cover 5.

Figure 3:
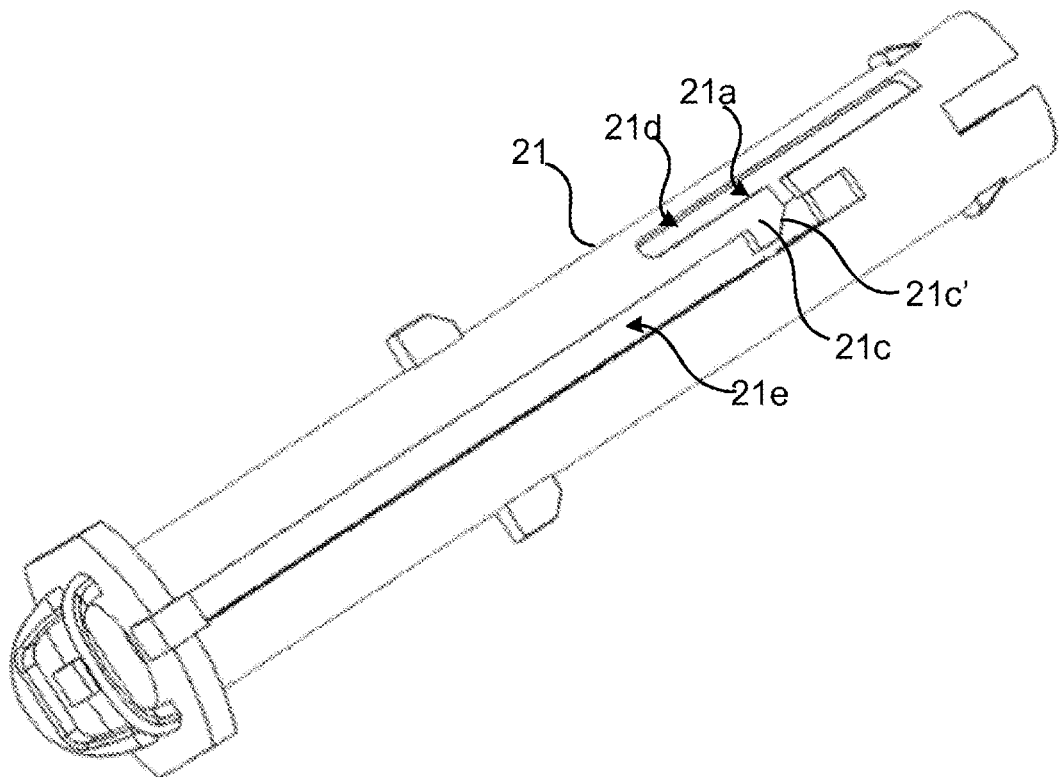
FIG. 3 shows a perspective view of an example of a plunger rod holder.
Figure 5A:
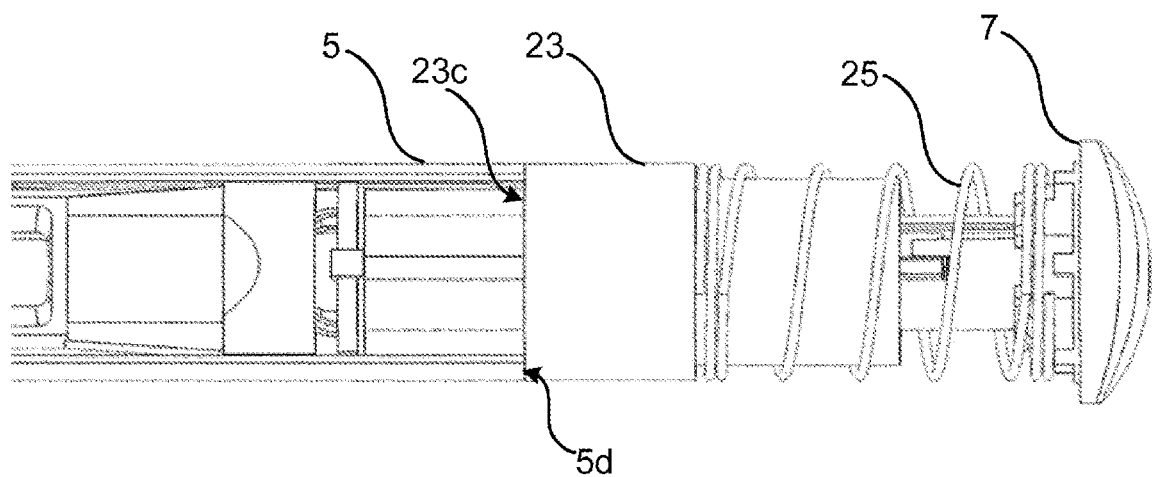
FIG. 5a shows a side view of an administration assembly in one state during operation.
Figure 5B:
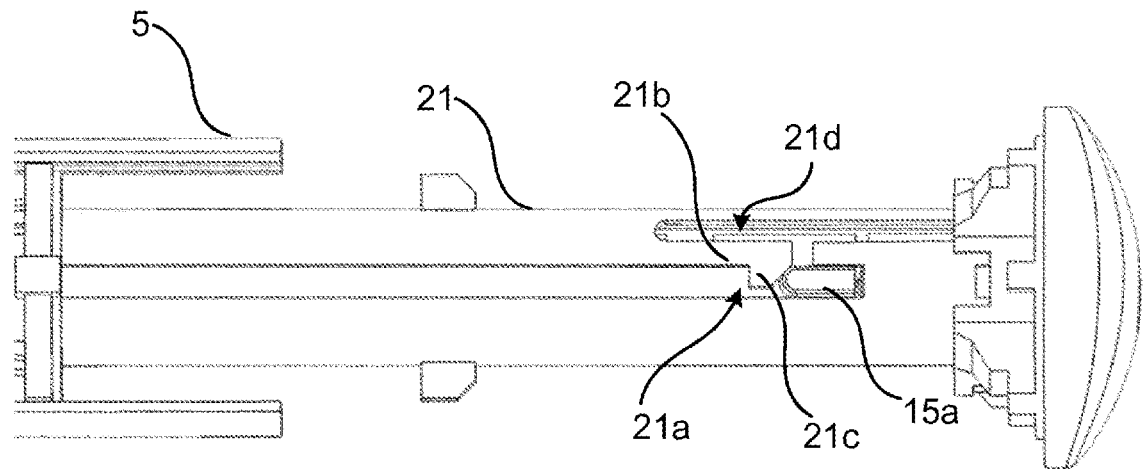
FIG. 5b shows a side view of an administration assembly in one state during operation.

Turning now to FIG. 3, the plunger rod holder 21 is shown. The first hold and release structure 21*a* comprises a distally extending first arm 21*b*, or tongue (FIG. 5*b*). The first arm 21*b* is flexible. The first arm 21*b* is formed between an axial first slot 21*d* and an axial second slot 21*e* arranged partly in parallel and overlapping with each other. The first arm 21*b* has a first tangential tab 21*c* having a distal end face 21*c*' which is bevelled in the tangential direction, and which extends into the second slot 21*e*. The first tangential tab 21*c* hence reduces the tangential dimension or width of the second slot 21*e*.

The first slot 21*d* has an axial extension in the distal direction relative to the distal end face 21*c*' of the first tangential tab 21*c*, towards a distal end of the plunger rod holder 21. The second slot 21*d* extends further in the proximal direction relative to the proximal end of the first arm 21*b* towards the proximal end of the plunger rod holder 21.

Figure 4:
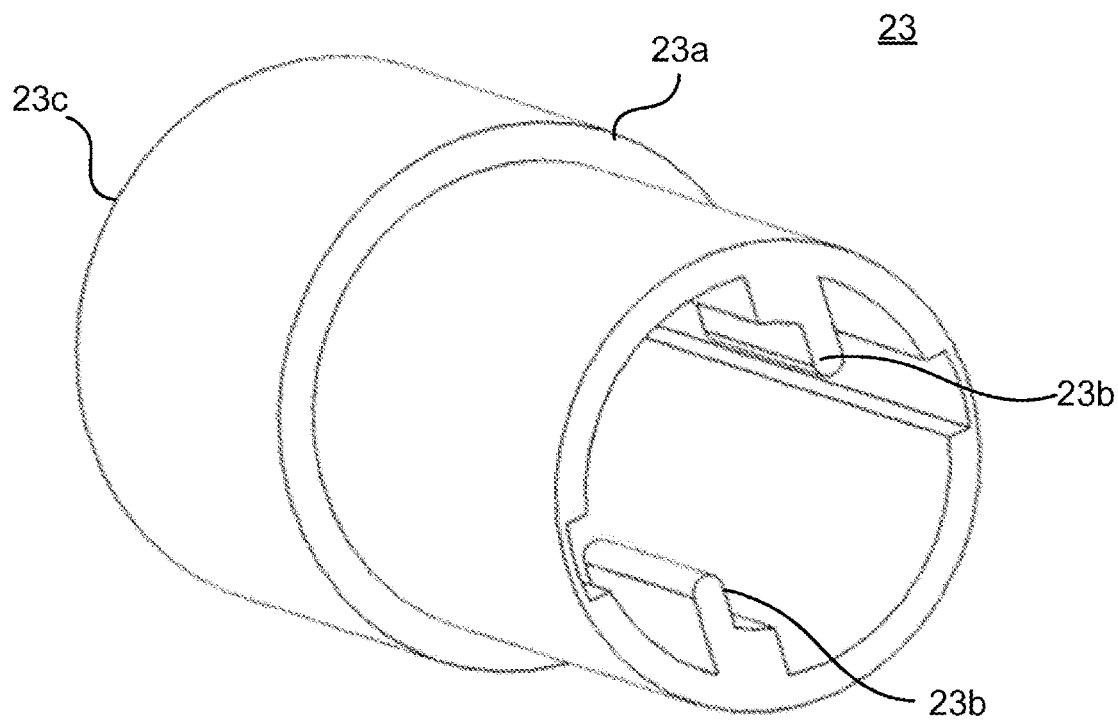
FIG. 4 depicts a perspective view of an activation sleeve.

FIG. 4 shows a perspective view of the activation sleeve 23. The activation sleeve 23 has an inner surface provided with an axially extending rib 23*b*. The axially extending rib 23*b* extends radially inwards. The axially extending rib 23*b* is configured to be slidably received by the first slot 21*d*, as will be explained in more detail below. It can be noted that in the example shown in FIG. 4, there are two axially extending ribs 23*b*, about 180 degrees apart. This is because there may be two first hold and release structures 21*a*, one for each of the axially extending ribs 23*b*, to increase the robustness of the administration assembly 10. There may hence be provided two second hold and releases structures 15*a*, each configured to cooperate with a respective first hold and release structure 21*a*.

The operation of the administration assembly 10 will now be described with reference to FIGS. 5*a*-8*b*. In FIG. 5*a*, the medicament delivery device 1, and thus the administration assembly 10, is in a default state, prior to the administration of a medicament. The housing 3 has been removed to expose the components contained inside the housing 3. In the default state, the delivery member cover 5 is in the extended position relative to the housing 3. The delivery member cover 5, in particular the distal end 5*d* thereof, bears against the activation sleeve 23, in particular the proximal end 23*c* thereof. In this state, the second resilient member 25 is in a non-compressed state, or at least only slightly compressed.

FIG. 5*b* shows the default state with the activation sleeve 23 and the second resilient member 25 removed. The second hold and release structure 15*a* is axially aligned with and bears against the first hold and release structure 21*a*. In particular, the protrusion 15*a*, which is arranged distally with respect to the first tangential tab 21*c*, bears against the first tangential tab 21*c*. The protrusion 15*a* has a proximal end bearing against the distal end face 21*c*' of the first tangential tab 21*c*. Although the first arm 21*b* is flexible it is unable to move, because the axially extending rib 23*b* of the activation sleeve 23 is arranged in the first slot 21*d*, preventing the first arm 21*b* to flex in the tangential or circumferential direction of the plunger rod holder 21. The first hold and release structure 21*a* is hence in the axially locking contact position with the second hold and release structure 15*a*.

Figure 6A:
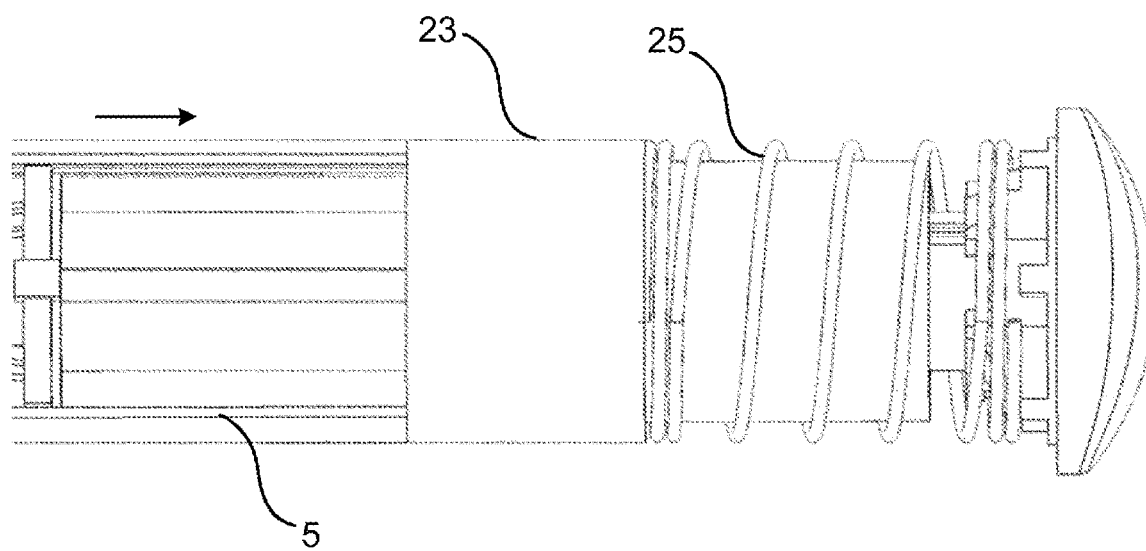
FIG. 6a shows a side view of an administration assembly in one state during operation.

In FIG. 6*a*, the delivery member cover 5 has been moved in the distal direction from the extended position relative to the housing 3 towards the retracted position. This movement of the delivery member cover 5 has concurrently moved the activation sleeve 23 in the distal direction, causing the second resilient member 25 to become more compressed than in the default position described above.

Figure 6B:
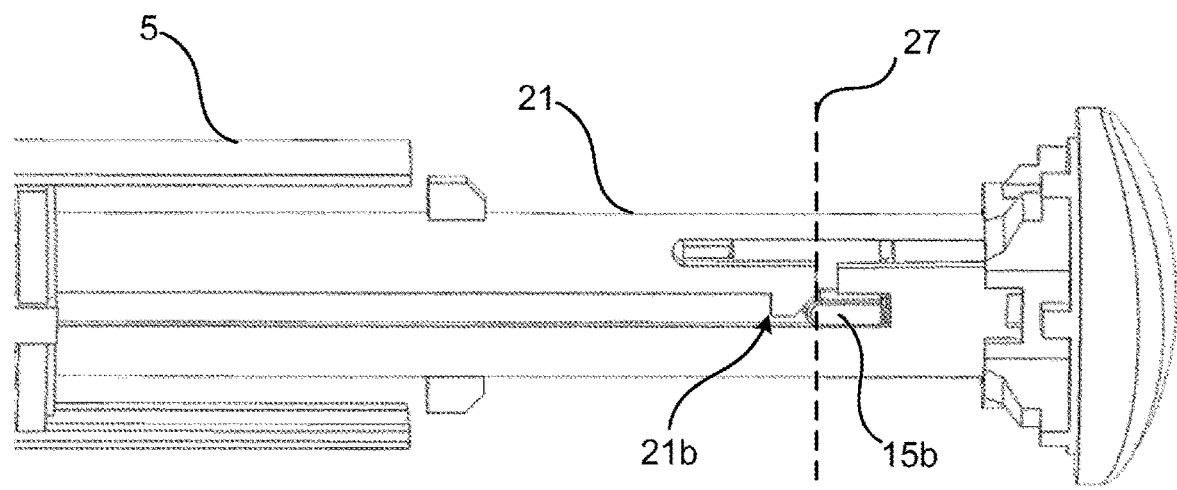
FIG. 6b shows a side view of an administration assembly in one state during operation.

FIG. 6*b* shows the same situation as in FIG. 6*a* but with the activation sleeve 23 and the second resilient member 25 removed. Although not shown, the trailing edge, or proximal edge, of the axially extending rib 23*b* of the activation sleeve 23 has not moved past an activation position indicated by numeral 27.

Figure 7A:
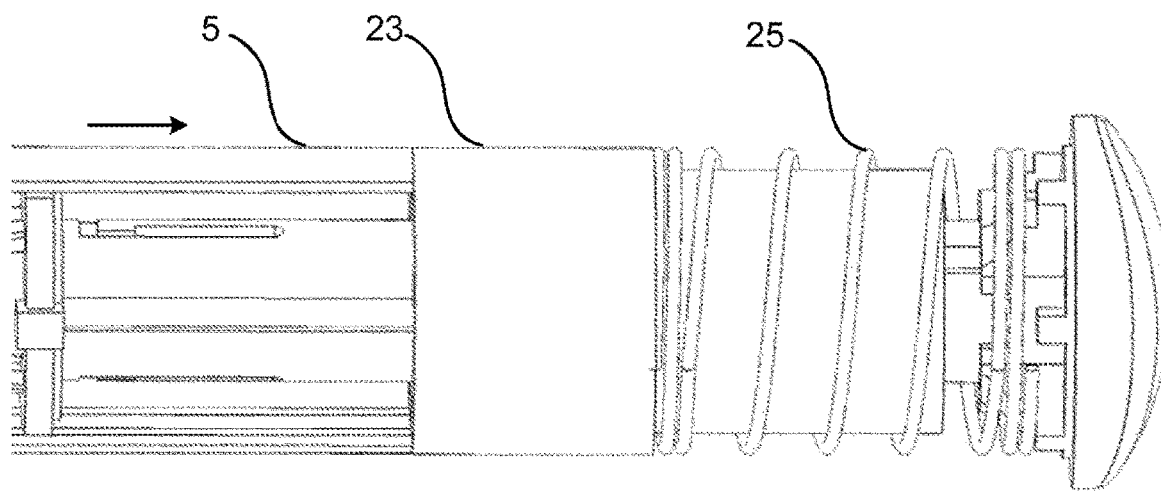
FIG. 7a shows a side view of an administration assembly in one state during operation.
Figure 7B:
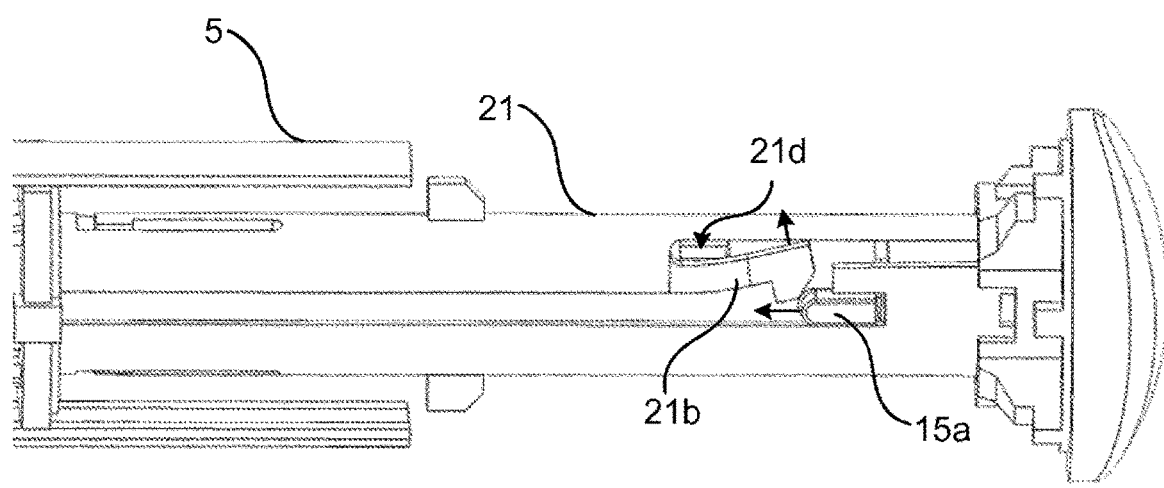
FIG. 7b shows a side view of an administration assembly in one state during operation.

In FIG. 7*a* the delivery member cover 5 has been moved even further in the distal direction towards the retracted position. This movement of the delivery member cover 5 has concurrently moved the activation sleeve 23 in the distal direction to the release position. In the situation shown in FIG. 7*a*, the trailing edge, or proximal edge, of the axially extending rib 23*b* has moved past the activation position 27. The first arm 21*b* is thus allowed to flex into the first slot 21*d*. In FIG. 7*b*, it can be seen that the first arm 21*b* is flexed in the tangential direction, into the first slot 21*d*, due to the proximal biasing provided by the second hold and release structure 15*a*, i.e. by the protrusion.

Figure 8A:
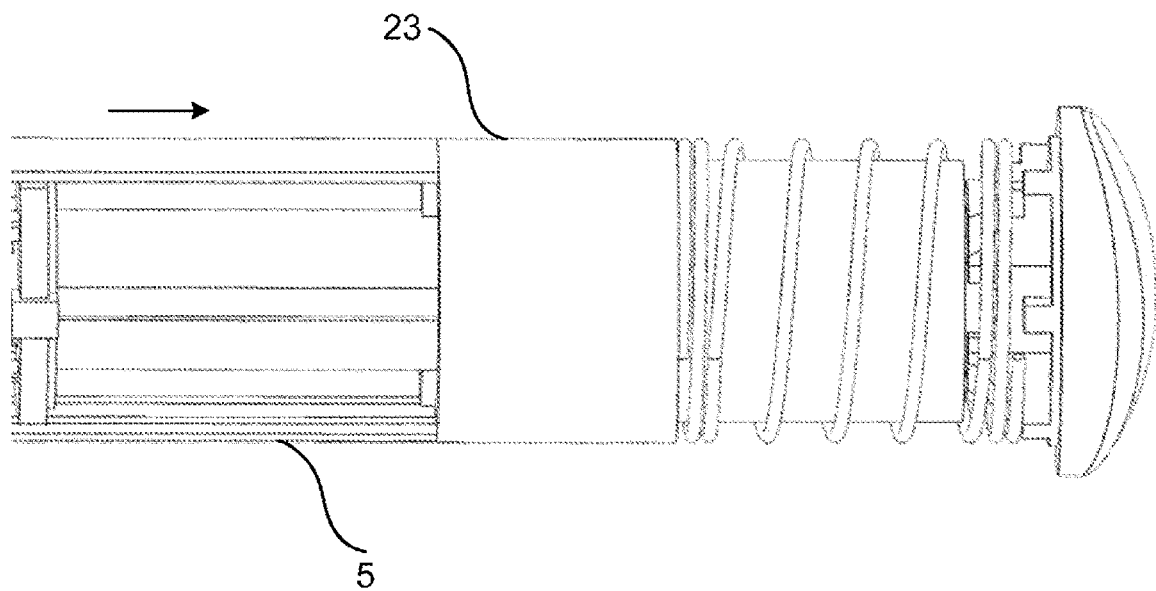
FIG. 8a shows a side view of an administration assembly in one state during operation.
Figure 8B:
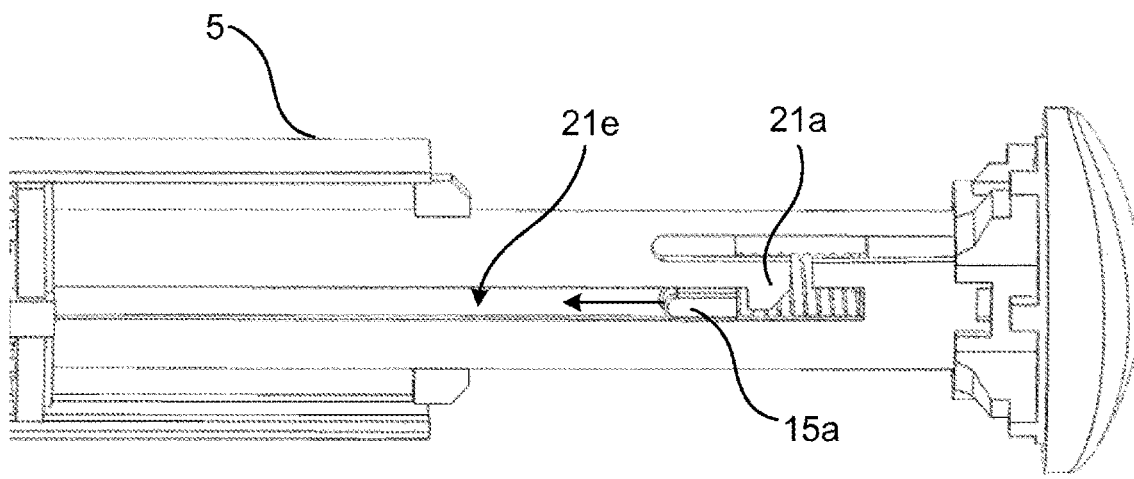
FIG. 8b shows a side view of an administration assembly in one state during operation.

In FIG. 8*a*, the delivery member cover 5 has reached the retracted position. FIG. 8*b* shows that the second hold and release structure 15*a*, the protrusion, has moved past the first tangential tab 21*c* in the proximal direction. The first tangential tab 21*c* has thus flexed back to its default position. Since the second hold and release structure 15*a* has moved past the first tangential tab 21*c*, the plunger rod 15 will now be moved forward, i.e. in the proximal direction due to the proximal biasing provided by the first resilient member 17. Since the second hold and release structure 15*a*, i.e. the protrusion, is received by the second slot 21*e*, their cooperation will ensure that the plunger rod 15 will move proximally without rotation relative to the plunger rod housing 21. The second hold and release structure 15*a* may hence define a guiding structure in the form of the radially outwards extending protrusion indicated by numeral 15*a*.

Figure 9:
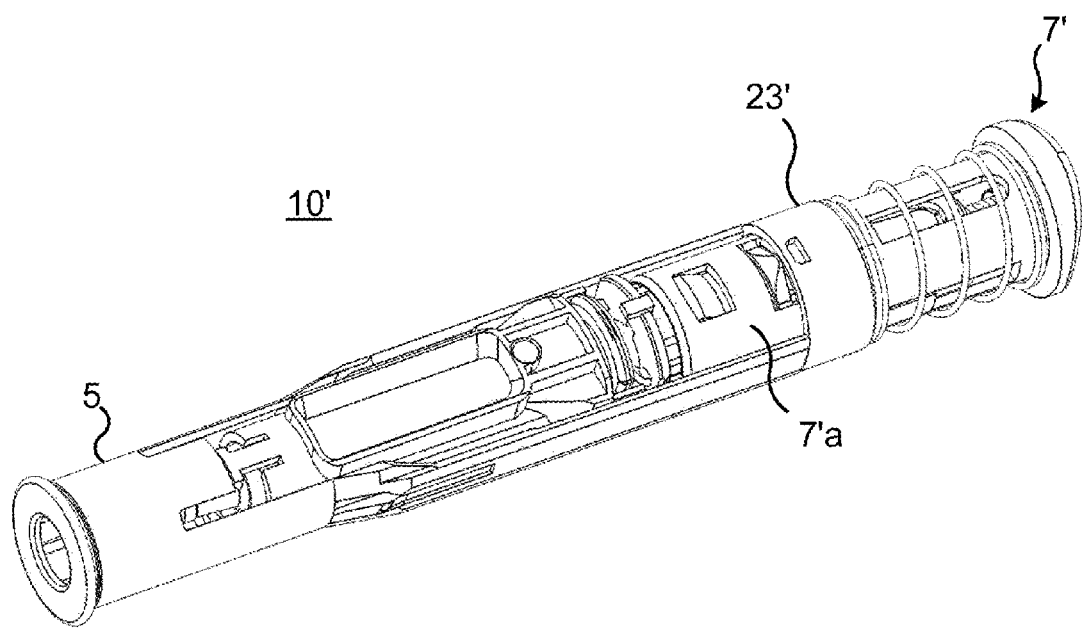
FIG. 9 is a perspective view of another example of an administration assembly.

FIG. 9 shows a perspective view of another example of an administration assembly 10' similar to the previously described one. The administration assembly 10' includes the same main components as the previous example, namely a triggering member, again exemplified by a delivery member cover 5, an activation sleeve 23', and rear end cap 7'. The rear end cap 7' has a tubular body 7'*a*. The delivery member cover 5 is configured to move the activation sleeve 23' from its first position towards its second position in the same manner as described above.

Figure 10:
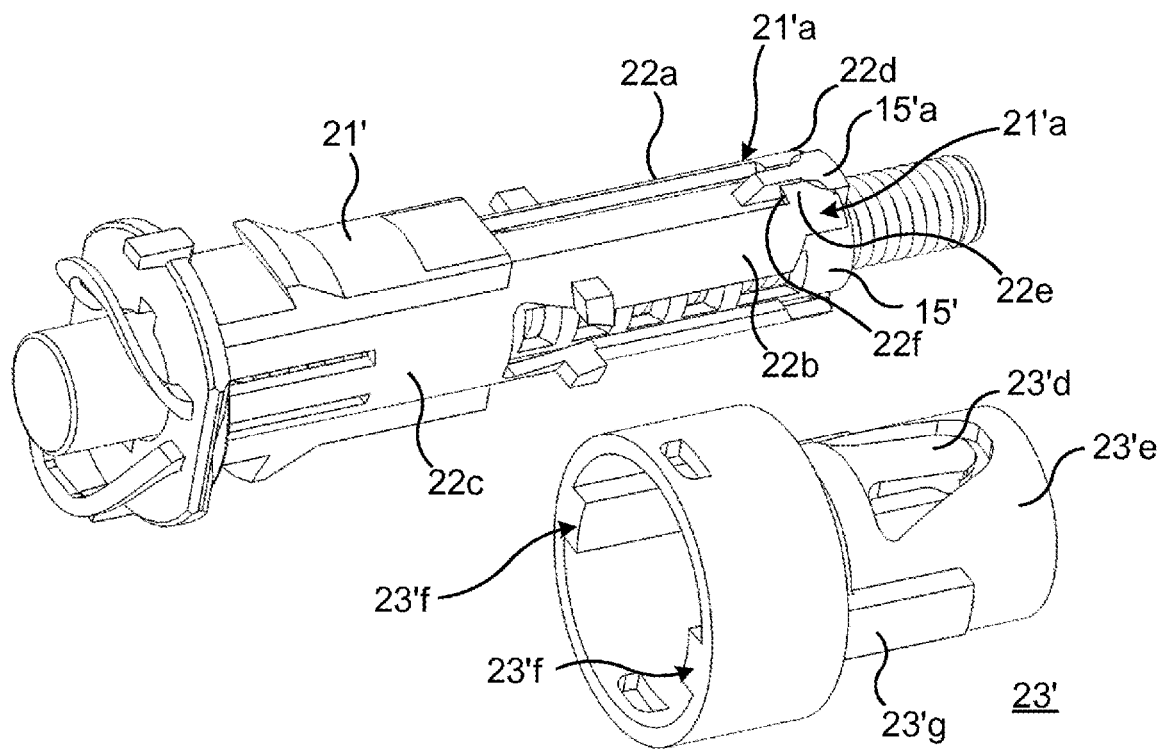
FIG. 10 shows perspective view of a certain components of the administration assembly in FIG. 9.

Turning now to FIG. 10 a perspective view of a plunger rod holder 21', a plunger rod 15' and the activation sleeve 23' of the administration assembly 10' are shown. The plunger rod 15' is received by the plunger rod holder 21'. The plunger rod holder 21' has a first hold and release structure 21'*a*, which comprises a first arm 22*a* and a second arm 22*b* extending parallel with each other. The first arm 22*a* and the second arm 22*b* extend in the distal direction from their attachment with the main body 22*c* of the plunger rod holder 21'. Each of the first arm 22a and the second arm 22b has a tangential extension which is typically less than 90 degrees. To this end, the circumferential or tangential extension of each of the first arm 22a and the second arm 22b is typically less than one fourth of a turn in the circumferential direction of the plunger rod holder 21'. The plunger rod holder 21' may for instance be provided with four arms in total, which is the case in the present example. Each arm, e.g. the first arm 22a and the second arm 22b, may be connected to the main body 22c of the plunger rod holder 21' by means of living hinges. Each of the first arm 22a, the second arm 22b, and the two remaining arms, may due to their slender nature be flexible in the tangential direction.

Although there may be in total four arms provided, only the first and the second arm 22a, 22b, which form a first arm pair, will be described in more detail in the following. The third and the fourth arm form a second arm pair. The structure of all the arms is the same.

The first arm 22a comprises a first tangential tab 22d and the second arm comprises a second tangential tab 22e. The first and second tangential tabs 22d and 22e extend towards each other in the tangential direction. The tangential distance between the first arm 22a and the second arm 22b hence decreases between the two tangential tabs 22d and 22e.

The plunger rod 15' comprises a second hold and release structure 15'a, which in the present example comprises a radially outward extending protrusion or wing. The first and second tangential tabs 22d and 22e are configured to cooperate with the radially outwards extending protrusion. In particular, two tangential tabs 22d and 22e are configured to block proximal movement of the radially outwards extending protrusion and thus of the plunger rod 15' when the activation sleeve 23' is in the first position. The distance between the two tangential tabs 22d and 22e is too small for the radially outwards extending protrusion to pass between. The plunger rod 15' is hence maintained in an axially locked position with the plunger rod holder 21' when the activation sleeve 23' is in the first position.

Figure 11:
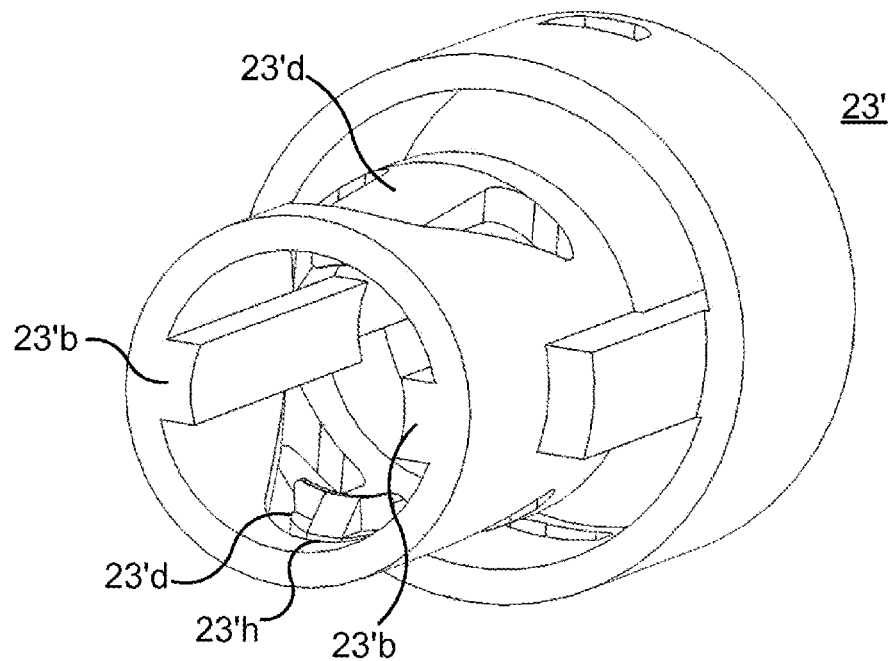
FIG. 11 is a perspective view of an activation sleeve of the administration assembly in FIG. 10.

The activation sleeve 23' is tubular and has an inner surface provided with axially extending ribs 23'f. Axially extending ribs 23'b are provided inside the distal portion 23'e of the activation sleeve 23', as shown in FIG. 11. The axially extending ribs 23'f and 23'b are configured to run between the first arm pair and the second arm pair. In particular, the first arm 22a and the second arm 22b are prevented from tangential movement as long as the axially extending ribs 23'b inside the distal portion 23'e of the activation sleeve 23' run between the first arm pair and the second arm pair. Once these axially extending ribs 23'b move distally beyond the first arm 22a and the second arm 22b and out from their position between the first arm pair and the second arm pair, when the activation sleeve 23' has been moved sufficiently in the distal direction from the first position towards the second position, the biasing of the plunger rod 15' and the contact between the radially outwards extending portion and the two tangential tabs 22d and 22e, will force the first arm 22a and the second arm 22b to move in the tangential direction. The inner diameter of the distal portion 23'e cannot accommodate any substantial radial movement of the first arm 22a and the second arm 22b. The distance between the opposing first tangential tab 22d and the second tangential tab 22e will thus increase, allowing the radially outwards extending portion to pass between. The plunger rod 15' is thus released from engagement with the plunger rod holder 21'.

The activation sleeve 23' also has outer axial ribs 23'g configured to run in corresponding slots in the tubular body 7'a of the rear end cap 7'. The activation sleeve 23' is thereby prevented from rotation relative to the rear end cap 7'. Since the activation sleeve 23' has the axially extending ribs 23'b and 23'f running between the first arm pair and the second arm pair of the plunger rod holder 21', the plunger rod holder 21' is also prevented to rotate relative to the rear end cap 7'. Additionally, the plunger rod 15' is rotationally locked relative to the plunger rod holder 21' since the radially outwards extending protrusion is configured to run in the space between the first arm 22a and the second arm 22b. The radially outwards extending protrusion hence forms a guiding structure to prevent rotation of the plunger rod 15' relative to the plunger rod holder 21'. All of the above-described components are hence prevented to rotate relative to the housing of the medicament delivery device in which they are mounted.

The activation sleeve 23' has a radially flexible tongue 23'd configured to lock the activation sleeve 23' in the first position when it has returned by biasing force to the first position. The delivery member cover 5 will thus not be able to move into the housing 3 from the extended position to the retracted position after medicament expulsion has been provided. The radially flexible tongue 23'd is configured to bear against the radially outwards extending protrusion of the plunger rod 15' when the activation sleeve 23' is in the first position. The radially flexible tongue 23'd is configured to move over the radially outwards extending protrusion 23'd when moved from the first position towards the second position. Due to the biasing provided by the second resilient member 25, shown in the example in FIG. 2, the activation sleeve 23' is returned to the first position once the pressure on the delivery member cover 5 is released, i.e. when medicament delivery has been finalised and the medicament delivery device is moved from the site of activation. The radially flexible tongue 23'd has a radially inwards extending protrusion 23'h, shown in FIG. 11. When the activation sleeve 23' returns to the first position, this radially inwards extending protrusion 23'h will be arranged proximally with respect to a radial heel 22f, shown in FIG. 10 and prevent the activation sleeve 23' from being moved in the distal direction.

The operation of the administration assembly 10' will now be described in more detail with reference to FIGS. 12a-12d.

Figure 12A:
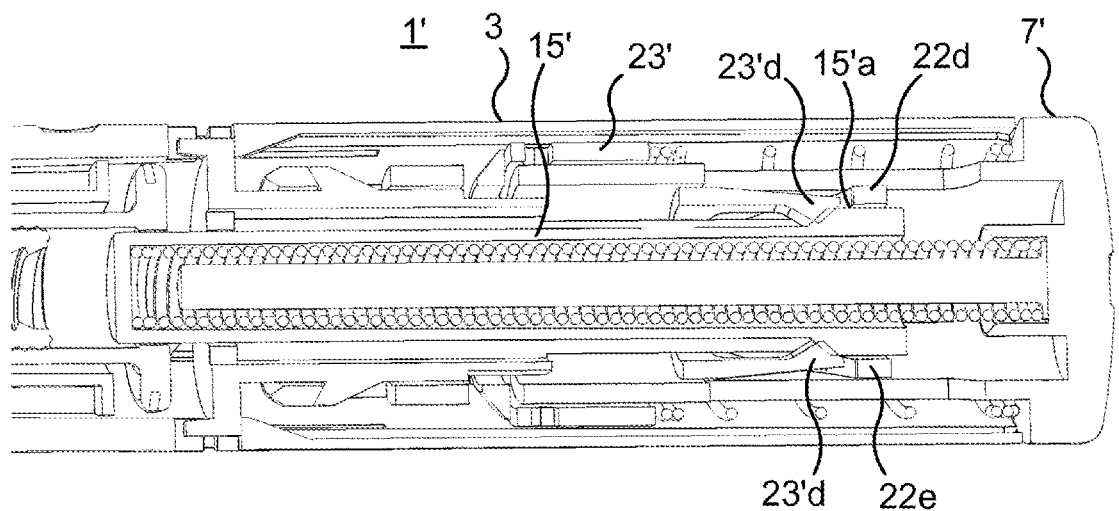
FIG. 12a shows a longitudinal section of a medicament delivery device including the administration assembly in FIG. 9 in one stage of operation.

In FIG. 12a a longitudinal section of a distal end portion of a medicament delivery device 1' comprising the administration assembly 10' is shown. The activation sleeve 23' is in the first position and the axially extending ribs 23'b are provided between the first arm pair and the second arm pair, preventing e.g. the first arm 22a and the second arm 22b from moving in the tangential direction. The second hold end release structure 15'a, including the radially outwards extending protrusion is thus not able to move past the two distal end tangential extending portions 22d and 22e.

Figure 12B:
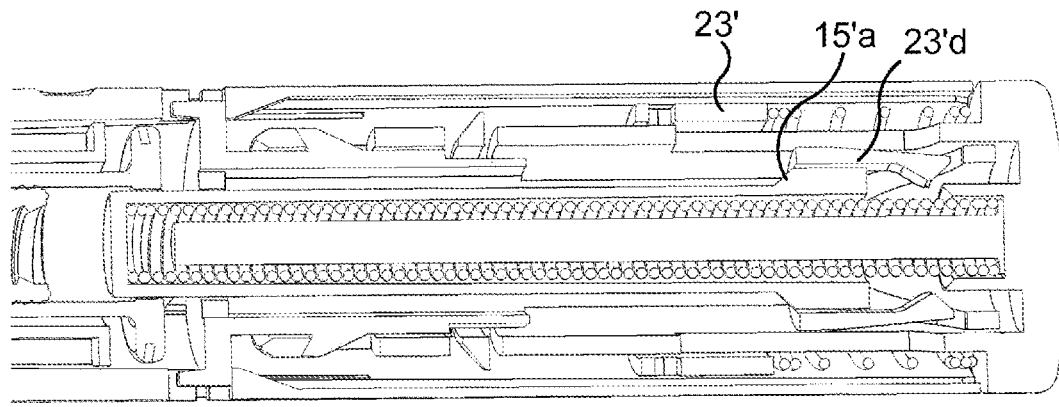
FIG. 12b shows a longitudinal section of a medicament delivery device including the administration assembly in FIG. 9 in another stage of operation.

In FIG. 12b the activation sleeve 23' has been moved in the distal direction towards the second position by the delivery member cover, which cannot be seen in this longitudinal section. The activation sleeve 23' has been moved to an activation position, which is where the axially extending ribs 23'b of the distal portion 23'e move out from between the first arm pair and the second arm pair. This allows the hinged first arm 22a and the second arm 22b to move tangentially, due to the force acting thereon by the biased radially outwards extending portion of the plunger rod 15'.

Figure 12C:
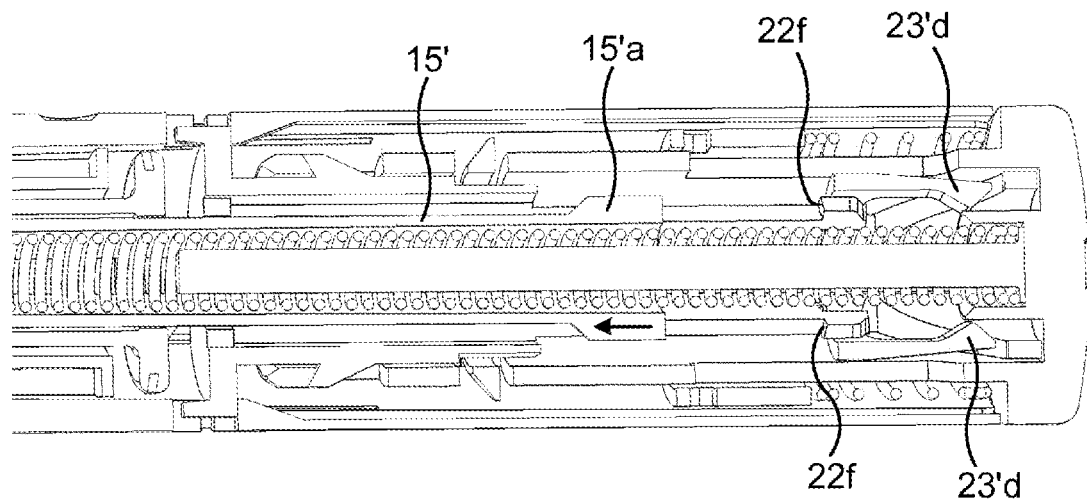
FIG. 12c shows a longitudinal section of a medicament delivery device including the administration assembly in FIG. 9 in another stage of operation.

In FIG. 12c the activation sleeve 23' is in the second position, the first arm 22a and the second arm 22b have been moved in the tangential direction and the plunger rod 15' has thus been released from being axially locked with the plunger rod holder 21'. The plunger rod 15' has in particular been moved in the proximal direction as indicated by the arrow.

Figure 12D:
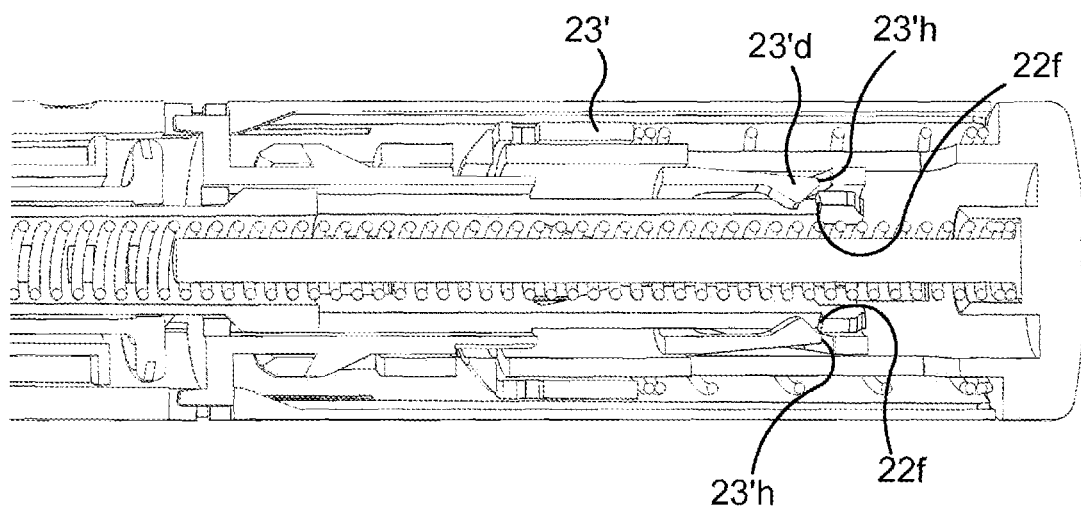
FIG. 12d shows a longitudinal section of a medicament delivery device including the administration assembly in FIG. 9 in another stage of operation.

In FIG. 12d, the medicament delivery device 1' has been moved from the site of administration and the proximally biased activation sleeve 23' has consequently returned to the first position. Since the plunger rod 15' has moved proximally into the medicament container, the radially flexible tongues 23'*d* and the radially inwards extending protrusions 23'*h* will obtain their default position, which is a radially deeper position compared to when the radially flexible tongues 23'*d* rested on the plunger rod 15' when the plunger rod 15' was in its initial position. The radially inwards extending protrusions 23'*h* of the two radially flexible tongues 23'*d* are located proximally relative to the radial heels 22*f* and facing the radial heels 22*f*, blocking distal movement of the activation sleeve 23'.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An administration assembly for a medicament delivery device, comprising:
    a plunger rod,
    a first resilient member configured to bias the plunger rod in a proximal direction,
    an elongated plunger rod holder configured to receive the plunger rod,
    an activation sleeve configured to receive a portion of the plunger rod holder, and configured to move axially from a first position relative to the plunger rod holder to a second position, wherein the activation sleeve is configured to be biased towards the first position, and
    wherein the plunger rod holder has a first hold and release structure and the plunger rod has a second hold and release structure, wherein in the first position the activation sleeve is configured to maintain the first hold and release structure in an axially locking contact position with the second hold and release structure in which the second hold and release structure is prevented from movement relative to the first hold and release structure, thereby locking the plunger rod axially relative to the plunger rod holder,
    wherein in the second position the activation sleeve is configured to allow the first hold and release structure to move from the axially locking contact position, whereby biasing of the plunger rod provided by the first resilient member causes the second hold and release structure to act with a proximally directed force on the first hold and release structure, moving the first hold and release structure tangentially from the axially locking contact position to thereby release the plunger rod from the plunger rod holder,
    wherein the first hold and release structure comprises a flexible arm having a first tangential tab that is adjacent to, axially aligned with, and proximally located relative to the second hold and release structure when in the axially locking contact position, wherein the second hold and release structure is a radially outwards extending protrusion, and
    wherein an inner surface of the activation sleeve further comprises an axially extending rib that extends radially inward such that the axially extending rib is positioned within a slot in the plunger rod holder such that the axial extending rib bears against the flexible arm when the activation sleeve is in the first position preventing movement of the flexible arm in a tangential direction.

2. The administration assembly as claimed in claim 1, comprising a second resilient member configured to bias the activation sleeve in the proximal direction towards the first position.

3. The administration assembly as claimed in claim 1, comprising a guiding structure configured to prevent the plunger rod to rotate relative to the plunger rod holder when released from the plunger rod holder.

4. The administration assembly as claimed in claim 3, wherein the second hold and release structure defines the guiding structure.

5. The administration assembly as claimed in claim 1, wherein the first tangential tab has a distal end face configured to cooperate with the second hold and release structure, wherein the distal end face of the first tangential tab is bevelled in the tangential direction.

6. The administration assembly as claimed in claim 1, wherein the axially extending rib is configured to move axially in a distal direction beyond the flexible arm in the second position of the activation sleeve, allowing the flexible arm to move in the tangential direction to thereby allow the second hold and release structure to move axially past the first tangential tab.

7. The administration assembly as claimed in claim 1, wherein the plunger rod holder has an axially extending second slot in which the second hold and release structure is configured to run in the proximal direction when the plunger rod has been released from the plunger rod holder.

8. The administration assembly as claimed in claim 1, wherein the first hold and release structure comprises a distally extending axial second arm extending parallel with the flexible arm, which second arm has a second tangential tab extending towards the first tangential tab, and wherein the radially outwards extending protrusion is configured to bear against and be located distally with respect to the first tangential tab and the second tangential tab when the activation sleeve is in the first position, the first tangential tab and the second tangential tab blocking proximal movement of the plunger rod.

9. The administration assembly as claimed in claim 8, wherein the activation sleeve comprises a plurality of axially extending ribs, wherein a first axially extending rib is configured to bear against the flexible arm and a second axially extending rib is configured to bear against the second arm in the first position of the activation sleeve to prevent tangential movement of the flexible arm and the second arm, the first axially extending rib and the second axially extending rib being configured to move axially in a distal direction beyond the flexible arm and the second arm in the second position of the activation sleeve, allowing the flexible arm and the second arm to move in the tangential direction to thereby allow the radially outwards extending protrusion to move axially past the first tangential tab and the second tangential tab.

10. A medicament delivery device comprising: a housing, a triggering member configured to move the activation sleeve from the first position towards the second position, and an administration assembly as claimed in claim 1 configured to be received by the housing.

11. A medicament delivery device according to claim 10, wherein the triggering member is a delivery member cover having a distal end configured to bear against a proximal end of the activation sleeve.

12. An administration assembly for a medicament delivery device, comprising:
- a plunger rod;
- a first resilient member positioned inside the plunger rod, where the first resilient member engages an inside surface of the plunger rod to bias the plunger rod in the proximal direction;
- an elongated plunger rod holder configured to receive the plunger rod: and
- an activation sleeve configured to receive a portion of the plunger rod holder, and configured to move axially from a first position relative to the plunger rod holder to a second position, wherein the activation sleeve is biased towards the first position by a second resilient member,
- wherein the plunger rod holder has a first hold and release structure and the plunger rod has a radially protruding second hold and release structure, wherein in the first position the activation sleeve maintains the first hold and release structure in an axially locking contact position with the second hold and release structure such that the second hold and release structure is prevented from moving axially relative to the first hold and release structure and locking the plunger rod axially relative to the plunger rod holder,
- wherein in the second position the activation sleeve allows the first hold and release structure to move circumferentially relative to the plunger rod from the axially locking contact position to a release position which causes the second hold and release structure to engage and move the first hold and release structure tangentially from the axially locking contact position thereby releasing the plunger rod from the plunger rod holder such that the plunger rod can move axially in a proximal direction,
- wherein the first hold and release structure comprises a flexible arm having a first tangential tab that is adjacent to, axially aligned with, and proximally located relative to the second hold and release structure when in the axially locking contact position, and
- wherein an inner surface of the activation sleeve further comprises an axially extending rib that extends radially inward such that the axially extending rib is positioned within a slot in the plunger rod holder such that the axially extending rib bears against the flexible arm when the activation sleeve is in the first position preventing movement of the flexible arm in a tangential direction.

13. The administration assembly of claim 12, further comprising a second resilient member configured to bias the activation sleeve in the proximal direction towards the first position.

14. The administration assembly of claim 12, wherein the first tangential tab further comprises a distal end face that cooperates with a proximal end of the second hold and release structure, where the distal end face is beveled in the tangential direction.

15. The administration assembly of claim 12, wherein the axially extending rib moves axially in a distal direction as the activation sleeve moves from the first position to the second position, where the axial movement of the axially extending rib allows the flexible arm to move in the tangential direction and allows the second hold and release structure to move axially past the first tangential tab.

16. The administration assembly of claim 12, wherein the second hold and release structure is slidably positioned within an axially extending second slot in the plunger rod holder when the plunger rod has been released from the plunger rod holder.

* * * * *